United States Patent [19]

Boutevin et al.

[11] Patent Number: 5,527,933

[45] Date of Patent: Jun. 18, 1996

[54] METHOD FOR PREPARING A HYBRID ORGANODISILANOL AND POLYMERS THEREOF

[76] Inventors: Bernard Boutevin, Les Terres Blanches, 1 rue Anselme Mathieu, 3400 Montpellier; Francine Guida-Pietrasanta, 31, Avenue du professeur Grasset, 34000 Montpellier; Amedee Ratsimihety, E.N.S.C.M.-8, rue de l'Ecole Normale, 34053 Montpellier Cedex 1, all of France; Gerardo Caporiccio, Via Emanuele Filiberto, 13, 20149 Milano, Italy

[21] Appl. No.: 537,597

[22] Filed: Oct. 2, 1995

[30] Foreign Application Priority Data

Apr. 6, 1995 [IT] Italy ............................... MI95A0701

[51] Int. Cl.$^6$ ....................................... C07F 7/08
[52] U.S. Cl. ...................... 556/431; 556/435; 556/445; 556/449
[58] Field of Search ........................... 556/431, 435, 556/445, 449

[56] References Cited

U.S. PATENT DOCUMENTS

| | | | |
|---|---|---|---|
| 2,561,429 | 7/1951 | Sveda | 260/448.2 |
| 3,188,336 | 6/1965 | Haszeldine | 260/448.2 |
| 3,627,801 | 12/1970 | Pierce | 260/448.2 |
| 5,032,636 | 7/1991 | Ono | 524/265 |
| 5,041,588 | 8/1991 | Caporiccio | 556/413 |
| 5,110,973 | 5/1992 | Caporiccio | 556/488 |
| 5,453,528 | 9/1995 | Boutevin et al. | 556/431 |
| 5,475,078 | 12/1995 | Sato et al. | 556/431 X |

OTHER PUBLICATIONS

Applied Polymer Symposium No. 22, 103–125 (1973).
J. Fluorine Chem., (1971/72) 193–202.
J. Polym. Sci. Part A–1 (1972), vol. 10, pp. 947–953
Macromolecules 1994, 27, 1068–1070.
Journal of Fluorine Chemistry, 60 (1993) 211–223.

*Primary Examiner*—Paul F. Shaver
*Attorney, Agent, or Firm*—Alexander Weitz

[57] ABSTRACT

There is disclosed an improved method for preparing a hybrid organodisilanol compound having the formula $$HO-R^1R^2SiC_nH_{2n}RC_nH_{2n}SiR^1R^2-OH \quad (I)$$

said method comprising:

(A) reacting a dihydridosilane of the formula $$R^1R^2SiH_2 \quad (II)$$

with a diene of the formula $$C_nH_{2n-1}RC_nH_{2n-1} \quad (III)$$

to provide a dihydrido compound of the formula $$H-R^1R^2SiC_nH_{2n}RC_nH_{2n}SiR^1R^2-H \quad (IV); \text{ and}$$

(B) reacting said dihydrido compound (IV) with a buffered water solution in the presence of a palladium catalyst.

16 Claims, No Drawings

METHOD FOR PREPARING A HYBRID ORGANODISILANOL AND POLYMERS THEREOF

FIELD OF THE INVENTION

The present invention relates to a method for preparing a hybrid organodisilanol and hybrid siloxane polymers thereof. More particularly, the invention relates to the method wherein a dihydridosilane is used to hydrosilate a diene to provide a dihydrido compound which, in turn, is reacted with a buffered water solution in the presence of a palladium catalyst to prepare the hybrid organodisilanol, which is condensed to form a hybrid sila-organo-siloxane polymer or copolymer.

BACKGROUND OF THE INVENTION

Hybrid polymers comprising units, e.g., of the type $$\{-Me_2SiC_6H_{12}SiMe_2O-\} \tag{i}$$

wherein Me hereinafter denotes a methyl radical, are known in the art. Their preparation generally includes the following steps: A silane is prepared according to chemical equation (1):

$$Me_2SiH_2 + Me_2SiCl_2 \rightarrow 2\ Me_2Si(Cl)H \tag{1}$$

wherein the reaction is carried out in the presence of, e.g, tetraisobutylammonium bromide. The product of this reaction is then reacted in a hydrosilation reaction to endcap a vinyl or allyl-terminated compound, as represented by equation (2):

$$2\ Me_2Si(Cl)H + CH_2=CHC_2H_4CH=CH \rightarrow ClMe_2SiC_6H_{12}SiMe_2Cl \tag{2}$$

in which the reaction is carried out in the presence of a platinum catalyst. The resultant chlorine-terminated compound is then hydrolyzed and condensed to form the corresponding hybrid sila-organo-siloxane polymer (i). Of course, the above hydrolysis can also be accomplished in the presence of another diorganodichlorosilane and these mixtures may be condensed to provide copolymers. It has been observed that, even though the reaction represented by equation (2) is relatively efficient (yield is in the range of 80 to 90%), the reaction according to equation (1) is relatively inefficient (yields observed are only in the 40% to 60% range). The overall yield for the formation of the hydrolysis products is therefore in the general range of 32 to 54%. And, since the polymers and copolymers produced from these hydrolyzates have utility in such diverse applications as lubricants, rubbers and sealants, there is motivation to improve the process for their manufacture.

SUMMARY OF THE INVENTION

The present inventors have discovered an improved method which can be employed in the production of the above mentioned hybrid polymers. The instant method results in an improved overall yield for the preparation of a hybrid organodisilanol compound which is a precursor to the hybrid sila-organo-siloxane polymer.

The invention therefore relates to a method for preparing a hybrid organodisilanol compound having the formula $$H-\{OR^1R^2SiC_nH_{2n}RC_nH_{2n}SiR^1R^2\}-OH \tag{I}$$

wherein $R^1$ and $R^2$ denote monovalent organic groups, R represents a divalent organic group and n is 2 or 3. The compound represented by formula (I) is prepared by first reacting a dihydridosilane of the formula $$R^1R^2SiH_2 \tag{II}$$

with a diene of the formula $$C_nH_{2n-1}RC_nH_{2n-1} \tag{III}$$

to provide a dihydrido compound of the formula $$H-\{R^1R^2SiC_nH_{2n}RC_nH_{2n}SiR^1R^2\}-H \tag{IV}$$

The dihydrido compound (IV) is then reacted with a buffered water solution in the presence of a palladium catalyst to prepare the hybrid organodisilanol compound of the invention.

The invention also relates to particular polymers and copolymers based on the above hybrid organodisilanol (I) which unexpectedly exhibit a very low glass transition temperature and are free of any first order transition phenomena at temperatures greater than −30° C.

The present invention has been described in Italian Patent Application No. MI95 A 000701, filed Apr. 6, 1995, the specification of which is hereby incorporated by reference.

DETAILED DESCRIPTION OF THE INVENTION

In the above formulae, n is 2 or 3 and $C_nH_{2n-1}-$ represents a linear monovalent radical selected from the group consisting of $-CH=CH_2$ and $-CH_2-CH=CH_2$. $R^1$ and $R^2$ in these formulae each independently represents a monovalent organic group which is selected from the group consisting of alkyl radicals having 1 to 12 carbon atoms, phenyl, halogenated alkyl radicals having 3 to 12 carbon atoms, such as 3,3,3-trifluoropropyl, and alkylphenyl radicals wherein the alkyl radicals have 1–4 carbon atoms. When this group is a halogenated alkyl, the halogen substitution must not be on the alpha or beta carbon atom with respect to the silicon atom (i.e., all halogen substitution must occur at least three carbon atoms away from the silicon atom).

The $R^1$ and $R^2$ groups can also be a monovalent radical derived from telomers or cotelomers of fluorinated organic monomers and is illustrated by such groups as:

(i) alkylene-terminated monovalent homotelomers selected from the group consisting of telomers of chlorotrifluoroethylene, tetrafluoroethylene, vinylidene fluoride, and trifluoroethylene;

(ii) cotelomers selected from the group consisting of cotelomers of chlorotrifluoroethylene and hexafluoropropene;

(iii) cotelomers of tetrafluoroethylene and one member selected from the group consisting of hexafluoropropene, 1-H-pentafluoropropene and 2-H-pentafluoropropene;

(iv) cotelomers of vinylidene fluoride and one member selected from said hexa- and pentafluoropropenes;

(v) cotelomers of tetrafluoroethylene and a perfluoroalkyl vinyl ether;

(vi) cotelomers of tetrafluoroethylene, chlorotrifluoroethylene, and a perfluoroalkyl vinyl ether; and (vii) cotelomers of tetrafluoroethylene, chlorotrifluoroethylene and hexafluoropropene.

The above telomers and cotelomers are bonded to the silicon atom by a divalent, linear, non-halogenated, alkylene radical containing 2, 3 or 4 carbon atoms. For the purposes of the present invention, there should be no more than one phenyl group per silicon atom in formulas (I), (II) and (IV).

In the above formulae, R denotes a divalent organic group which is preferably a group —O($C_tH_{2t}O$)$_m$— wherein t is an integer having a value of 2 to 12, preferably 2 to 6, and m is an integer having a value of 1 to 6, preferably 1 to 3. Most preferably the group R is selected from the structures
—O($C_2H_4O$)$_m$—,
—O($C_3H_6O$)$_m$—,
—O($C_4H_8O$)$_m$— and
—O($C_6H_{12}O$)$_m$—
which m has the above defined meaning.

R in the above formulae can also be a divalent group selected from branched or linear divalent hydrocarbon groups having 2 to 12 carbon atoms, preferably 2 to 8 carbons, branched or linear divalent fluorohydrocarbon groups, or derivatives of telechelic divalent telomers or cotelomers. The preferred telechelic divalent fluorinated telomers or cotelomers may be represented by the formula:

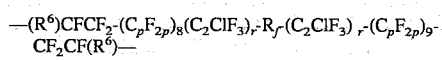

which $R_f$ represents a perfluoroalkylene radical containing from 2 to 6 carbon atoms, $R^6$ is fluorine or trifluoromethyl, the value of p is 2 or 3, r is 0 or a positive integer from 1 to 6, q is 0 or a positive integer from 1 to 6 and (r+q) is from 2 to 12.

The dienes of formula (III) which contain the above described preferred telechelic divalent fluorinated telomer or cotelomer R groups are known in the art and their preparation is illustrated in U.S. Pat. No. 5,110,973, which patent is assigned to the assignee of the present invention and is hereby incorporated by reference. Other dienes encompassed by formula (III) are also known in the art and description thereof is considered unnecessary.

The method of the present invention begins with the preparation of the dihydridosilane shown in formula (II). This is accomplished by reacting a diorganodihalosilane of the structure $R^1R^2SiQ_2$, in which $R^1$ and $R^2$ have their previously defined meanings and Q is chlorine or bromine, with an excess of lithium aluminum hydride (LiAlH$_4$). Preferably, the halogens of the diorganodihalosilane are chlorine and the reaction is carried out under reflux in a solvent (e.g., ethyl ether, tetrahydrofuran) and under an inert gas atmosphere (e.g., nitrogen). The yield for this reaction is quite high, generally in the range of about 90 to 95%.

The dihydridosilane (II) is then reacted with diene (III) in the presence of a hydrosilation catalyst to prepare the dihydrido compound (IV). At least two moles of (II) are used for each mole of (III). Preferably, an excess of the dihydridosilane (II) is used (e.g., 20% excess) to complete capping of the unsaturated ends of the diene. This reaction is also preferably carried out in a solvent, such as octane, hexane, toluene or xylene, and under an inert gas atmosphere such as argon, nitrogen or helium and preferably at a temperature of about 20° to 130° C. This reaction typically has a yield in the range of 80 to 90%.

The hydrosilation catalyst is exemplified by platinum catalysts, such as platinum black, platinum supported on silica micropowder, platinum supported on carbon powder, chloroplatinic acid, alcohol solutions of chloroplatinic acid, platinum/olefin complexes and platinum/alkenylsiloxane complexes, inter alia. In the present invention, this catalyst is preferably platinum supported on carbon. It is added in a catalytic quantity to promote the above hydrosilation reaction, typically in an amount sufficient to give 0.1 to 1,000 ppm (parts per million) by weight catalyst metal in the combination of components (II) and (III).

The dihydrido compound (IV) is then reacted with a buffered water solution in the presence of a palladium catalyst to prepare the hybrid organodisilanol (I). In this reaction, the amount of water employed should be sufficient to convert the SiH functionality of component (IV), and is preferably used in excess (e.g., up to 400% excess on a molar basis). Buffering the solution to maintain a slightly basic reaction environment is preferred in carrying out this reaction. Preferably, the reaction solution also contains a water-miscible solvent, such as dioxane or tetrahydrofuran, and is buffered with a basic salt or salt/base combination. The catalyst used in this reaction is preferably a powder which consists essentially of palladium on an alumina (i.e., $Al_2O_3$) support. This reaction typically has a yield in the range of about 90 to 95%.

The organodisilanol compound (I) prepared according to the method of the present invention may then be condensed, preferably in the presence of a basic catalyst, either with itself or, e.g., with a diorganosilane having the formula $$R^1R^2SiX_2 \qquad (V)$$

to form a homopolymer or a copolymer (i.e., a hybrid-sila-organo-polysiloxane), by methods well known in the art. In formula (V), $R^1$ and $R^2$ have their previously defined meanings and X is a hydrolyzable group, such as chlorine, alkoxy, oxime and acetoxy, among others. Thus, for example, when X is chlorine, an organodisilanol (I) can be co-condensed with a silane of the formula $R^1R^2SiCl_2$ or a silane of the formula $R^1R^3SiCl_2$, in which $R^1$ and $R^2$ have the above defined meanings and $R^3$ can be $R^1$ or an alkenyl radical such as vinyl, in the presence of a base such as pyridine, to form a copolymer consisting essentially of the respective siloxane units. When at least one of the siloxane units so employed contains a vinyl radical, the resulting copolymer can be crosslinked through this reactive functionality.

The types of polymers and copolymers contemplated herein include such systems as those represented by the formulae $(A)_x$, $(AB)_x$, $(ABA)_x$, $(BAB)_x$, in which —A— denotes the residue of compound (I) and has the formula

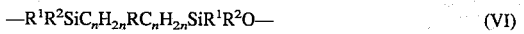

and —B— denotes the residue of siloxane units from compound (V) and has the formula

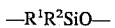

where $R^1$, $R^2$, R, and n have their previously defined meanings and the subscript x denotes the corresponding average degree of polymerization of each system which has a value ranging from 5 to 3,000, preferably from 10 to 1,000. Such repeating units $(A)_x$, $(AB)_x$, $(ABA)_x$, $(BAB)_x$ can be alternated with some more reactive units of the type $(Z)_w$ wherein Z represents the residue (—$R^1R^3SiO$—) in which $R^1$ and $R^3$ have their previously defined meanings and the ratio w/x is about 0.001 to 0.05.

The end groups of these polymers or copolymers can be any of the triorganosiloxy groups known in the art and these may be introduced by adding a capping agent in the above condensation step. Without such a capping component, the end groups would, of course, comprise the silanol groups inherently remaining after the condensation step. Examples of suitable end groups include trimethylsiloxy, dimethylphenylsiloxy and diethylphenylsiloxy, dimethylvinylsiloxy, dimethylhexenylsiloxy, dimethylhydroxysiloxy, dimethylhydrogensiloxy, dimethylalkoxysiloxy, methyldialkoxysiloxy and trialkoxysiloxy.

Of the systems described above, polymers or copolymers containing the unit $$—R^1R^2SiC_nH_{2n}RC_nH_{2n}SiR^1R^2O— \qquad \text{(VII)}$$

and, optionally, one or both of the following units $$—R^{1a}R^{2a}SiO— \qquad \text{(VIII)}$$

$$—R^{1a}R^{3a}SiO— \qquad \text{(IX)}$$

are believed to be novel. In formulae (VII) through (IX), $R^1$ and $R^2$ are identical or different $C_{1-C12}$ alkyl radicals, phenyl radical or $C_1-C_4$ alkyl-phenyl radicals; $—C_nH_{2n}—$ is a linear divalent radical wherein n is 2 or 3. In formula (VII), R is selected from the group consisting of:

a1) $—O(C_tH_{2t}O)_m—$ wherein t is an integer from 2 to 12, preferably from 2 to 6, m is an integer from 1 to 6, preferably from 1 to 3, preferably R is selected from the structures $—O(C_2H_4O)_m—$, $—O(C_3H_6O)_m—$, $—O(C_3H_6O)_m—$, $—O(C_6H_{12}O)_m—$ wherein m is from 1 to 3, with the proviso that no more than one phenyl group per silicon atom is present in the repeating unit (VII) and b1) branched or linear divalent hydrocarbon groups having from 2 to 8, preferably from 2 to 4, carbon atoms, with the proviso that, in the repeating unit (VII), no more than one phenyl group and no more than one methyl group per silicon atom is present and with the proviso that when $R^1$ is methyl then $R^2$ is selected from the group consisting of a $C_{5-C12}$ alkyl radical, phenyl radical and a $C_{1-C4}$ alkyl-phenyl radical.

In formulas (VIII) and (IX), $R^{1a}$ and $R^{2a}$ are independently selected from the group consisting of $C_{1-C12}$ alkyls, $C_{3-C12}$ halogenated alkyls, phenyl, $C_{1-C4}$ alkyl-phenyl and monovalent radicals derived from telomers or cotelomers of fluorinated organic olefins; $R^{3a}$ is an alkenyl radical such as vinyl.

The above novel hybrid siloxane polymers or copolymers include the systems
$(A)_x$, $(AB)_x$, $(ABA)_x$, $(BAB)_x$, wherein
—A— represents the unit of formula (VII);
—B— represents $—R^{1a}R^{2a}SiO—$ and/or $—R^{1a}R^{3a}SiO—$ units;
x represents the average degree of polymerization of each system and has a value ranging from 5 to 3,000, preferably from 10 to 1,000.

The applicants have unexpectedly found that the above novel systems have a very low glass transition temperature and are also free of any first order transition phenomena at temperatures greater than about −30° C. These properties are completely unexpected since it has been found, for example, that for the class of the hybrid tetramethyl-sila-alkylene-siloxanes where R is of the type (b1), discussed supra, and $R^1=R^2=—CH_3$, a first order transition appears evident near room temperature by differential scanning calorimetry (DSC) analysis. This means that these polymers or copolymers cannot be used at low temperatures. Thus, if the polymers or copolymers have the consistency of an oil at ambient conditions, they cannot be used as lubricants in low temperature applications since they become too viscous or heterogeneous. Similarly, if they have the consistency of a rubber, they cannot be used at low temperatures since they become brittle.

The above novel hybrid silicones obtained according to the present invention and containing the repeating unit of formula (VII) in which R is of the type (b1) have a glass transition temperature of −70° C. or less and do not exhibit the presence of any phenomena of first order transition at a temperature higher than −30° C. (e.g., by DSC at 10° C./min). It has also been unexpectedly found that the novel hybrid polymers or copolymers according to the present invention containing the recurring unit of formula (VII) in which R is a (poly)oxyalkylene group show a glass transition temperature much lower with respect to that of silicone oils known as silicone-glycol copolymers (see D. Klamann, Lubricants—Verlag Chemie Ed. 1984, page 140).

The polymers and copolymers of the present invention have very low glass transition temperatures and find utility in the preparation of lubricants, rubbers and sealants which are to be used at low temperatures. Thus, they may be employed in a method for lubricating a substrate such as a metal, or the interface between substrates, said method comprising applying the above polymer or copolymer to at least a portion of the substrate or interface. Similarly, they may be used to seal a joint formed between two or more structural members composed of metal, glass, ceramic, inter alia. When the polymers or copolymer of the present invention contain reactive groups, such as vinyl radicals, they may be formulated and cured to form rubber compositions which maintain their elasticity at low temperatures.

EXAMPLES

The following examples are presented to further illustrate the method of this invention, but are not to be construed as limiting the invention, which is delineated in the appended claims. All parts and percentages in the examples are on a weight basis and all measurements were obtained at 25° C., unless indicated to the contrary.

Example 1

Preparation of $(C_8H_{17})(CH_3)SiH_2$:

Methyl octyl dihydrosilane $(C_8H_{17})(CH_3)SiH_2$ (1a) was prepared from the corresponding dichlorosilane (912 g) by quantitative reduction with $LiAlH_4$ (160 g), at reflux in ether (3 liters) for 19 hours. The silane was distilled at 78° C. and 2.67 kPa (20 torr) and was characterized by IR absorption at 2132 cm$^{-1}$ and by $^{29}Si$ NMR, giving a peak centered at −33.5 ppm ($CDCl_3$), which confirmed the structure of the product as $(C_8H_{17})(CH_3)SiH_2$ (1a).

Hydrosilylation of $H_2C=CH—C_2H_4—CH=CH_2$ with $(C_8H_{17})(CH_3)SiH_2$:

The hydrosilylation was performed in a steel reactor. 0.486 g of dry 5% Pt/C and 3.44 g of n-octane were placed in the reactor, together with 21.2 g (0.135 mole) of $(C_8H_{17})(CH_3)SiH_2$ and 0.061 mole of 1,5-hexadiene. The reactor was sealed and the mixture was heated at 130° C. for 19 hours. After cooling, filtration and distillation, the telechelic hybrid dihydrosilane $$(H)Si(C_8H_{17})(CH_3)—C_6H_{12}—Si(C_8H_{17})(CH_3)H \qquad \text{(1b)}$$

was isolated by distillation at 175° C. and 5.3 Pa (4×10$^{-2}$ torr). Gas-liquid chromatography (GLC) performed on the impure product indicated a yield of about 90% on a weight basis.

Conversion of the hybrid dihydrosilane (1b) to the disilanol:

A flask (under argon) was charged with 0.5 g of dry 5% Pd/Al$_2$O$_3$, 50 ml of 1,4-dioxane and 4.5 ml of a buffer solution of NaH$_2$PO$_4$/H$_2$O and 0.1N NaOH and 0.025 mole of the hybrid dihydrosilane (1b) previously prepared was added. The mixture was heated at 30° to 40° C., for 24 hours. After cooling, it was diluted with 10 ml of diethylether, filtered and the solvent distilled off. The residue was identified as a telechelic hybrid-organo-disilanol of the structure $$\text{HOSi}(C_8H_{17})(CH_3)—C_6H_{12}—Si(C_8H_{17})(CH_3)(OH) \quad (1c)$$

which had a glass transition temperature of −70° C. The yield was about 90%. The product was also characterized by IR and NMR to confirm the above structure. Condensation of the hybrid disilanol and preparation of the hybrid-sila-organo-siloxane polymers.

A flask (under argon) was charged with 0.02 mole of the hybrid-organo-disilanol (1c) and 10 ml of anhydrous toluene and 4 drops of tetramethylguanidine trifluoroacetate were added. The mixture was heated in toluene at reflux (110° C.) for 19 hours. After cooling, it was washed with a 10% aqueous solution of NaHCO$_3$. The solvent was distilled off and the residue was identified as the hybrid silicone (yield= 95%). This resulting polymer of the structure $$\text{HO}—[Si(C_8H_{17})(CH_3)—C_6H_{12}—Si(C_8H_{17})—(CH_3)O]_n\text{H} \quad (1d)$$

had a glass transition temperature of −83° C. (differential scanning calorimetry at 10° C./minute) and any first order transition did not appear at DSC. A number average molecular weight of about 20,000 was measured (GPC in tetrahydrofuran using a polystyrene standard).

Example 2

In a procedure similar to that of Example 1, a diene of the structure $$\text{H}_2\text{C}=CH—C_6H_{12}—CH=CH_2 \quad (2a)$$

was reacted with the dihydrosilane (C$_8$H$_{17}$)(CH$_3$)SiH$_2$. The hydrosilylation was performed in a glass flask under argon using 0.243 g of dry 5% Pt/C and 1.72 g of n-octane along with 21.2 g (0.135 mole) of (C$_8$H$_{17}$)(CH$_3$)SiH$_2$ and 0.045 mole of 1,9-decadiene. The mixture was heated at 130° C. for 2 hours and, after cooling, another portion of 0.243 g Pt/C in 1.72 g of n-octane was added. The mixture was again heated at 130° C. for 12 hours and, after filtration and distillation, the hybrid dihydrosilane of the formula $$(\text{H})Si(C_8H_{17})(CH_3)—C_{10}H_{20}—Si(C_8H_{17})(CH_3)\text{H} \quad (2b)$$

was isolated by distillation. The yield of (2b) by GLC analysis of the undistilled product was about 90%.

The hybrid dihydrosilane (2b) was converted to the corresponding disilanol according to the procedure of Example 1 to provide a compound having a glass temperature of −70° C. with a confirmed structure $$\text{HOSi}(C_8H_{17})(CH_3)—C_{10}H_{20}—Si(C_8H_{17})(CH_3)(OH) \quad (2c)$$

The yield was 91%.

The above hybrid disilanol (2c) was condensed by the procedure of Example 1 to provide a polymer of the structure $$\text{HO}—[Si(C_8H_{17})(CH_3)—C_{10}H_{20}—Si(C_8H_{17})(CH_3)O]_n—\text{H} \quad (2d)$$

which polymer showed a glass transition temperature of −80° C.; a very small first order transition appeared at −50° C. A number average molecular weight of about 23,000 was measured and corresponds to an average degree of polymerization (DP) of 49.

A polymer similar to (2d), wherein the —C$_8$H$_{17}$ alkyl radical linked to each silicon atom of said formula is substituted by a methyl radical, shows a first order transition at about +10° C. and this polymer also has a higher glass transition temperature.

Example 3

Synthesis of CH$_2$=CH—CH$_2$—O—C$_6$H$_{12}$—O—CH$_2$—CH=CH$_2$:

1,6-hexanediol (HO—C$_6$H$_{12}$—OH) was reacted with a 150% excess of allyl chloride (ClCH$_2$—CH=CH$_2$) to provide a diene of the formula $$CH_2=CH—CH_2—O—C_6H_{12}—O—CH_2—CH=CH_2 \quad (3a)$$

The reaction was run at 40° C. for 19 hours in the presence of a tetrabutylammonium hydrogen sulfate (at 10% of the moles of the diol) and in the presence of a 50% aqueous NaOH solution, the latter material being used to neutralize the byproduct HCl. The yield of this reaction was about 91%. The diene (3a) had a boiling point of 85° C. at 20.3 kPa (0.2 mbar).

Synthesis of 
$$\text{H}—\underset{\underset{C_8H_{17}}{|}}{\overset{\overset{Me}{|}}{Si}}—C_3H_6—O—C_6H_{12}—O—C_3H_6—\underset{\underset{C_8H_{17}}{|}}{\overset{\overset{Me}{|}}{Si}}—\text{H}:$$

Diene (3a) was reacted with a 100% excess of a dihydrosilane of the formula Me(C$_8$H$_{17}$)SiH$_2$, wherein Me herein denotes a methyl radical. This silylation reaction was carried out under an argon atmosphere in the presence of a catalyst consisting of platinum supported on carbon, at 130° C. for 9 hours, as in Example 1. The resulting hybrid dihydro silane, obtained in about 90% yield, had the structure $$\text{H}—\underset{\underset{C_8H_{17}}{|}}{\overset{\overset{Me}{|}}{Si}}—C_3H_6—O—C_6H_{12}—O—C_3H_6—\underset{\underset{C_8H_{17}}{|}}{\overset{\overset{Me}{|}}{Si}}—\text{H} \quad (3b)$$

Analysis of (3b) was obtained as follows: IR: 2106 cm$^{-1}$ (SiH) $^1$H NMR (CDCl$_3$): 0.05 (d) (3H) SiCH$_3$; 0.6(4H)SiCH$_2$; 0.9(3H) CH$_2$CH$_3$; 1.3(12H) intermediate (CH$_2$)$_6$ of octyl; 1.6(m) (6H) SiCH$_2$CH$_2$ and OCH$_2$CH$_2$CH$_2$; 3.4(4H) OCH$_2$; 3.8(1H)SiH $^{29}$Si NMR (CDCl$_3$): −9.35 (s) ($^1$H irradiation) −9.35 (d) (without $^1$H irradiation)

Synthesis of 
$$\text{HO}—\underset{\underset{C_8H_{17}}{|}}{\overset{\overset{Me}{|}}{Si}}—C_3H_6—O—C_6H_{12}—O—C_3H_6—\underset{\underset{C_8H_{17}}{|}}{\overset{\overset{Me}{|}}{Si}}—\text{OH}:$$

The above hybrid dihydro silane (3b) was reacted with a buffered water solution using a 5% palladium supported on alumina catalyst. Again, 1,4-dioxane and the buffer solution of NaH$_2$PO$_4$/H$_2$O and 0.1N NaOH were used in the proportions given in Example 1. The mixture was heated at 30° to 40° C. for 24 hours and, after cooling, it was diluted with 10 ml of ether, filtered and solvent distilled off to provide a hybrid organo-disilanol of the structure

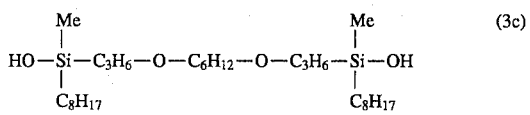

This disilanol compound was obtained in 92% yield, had a glass temperature of −82° C., and was characterized as follows:

IR: 3416 cm$^{-1}$ (SiOH) $^1$H NMR (CDCl$_3$): 0.1(s)(3H)SiCH$_3$; 0.6(4H) SiCH$_2$; 0.9(3H)CH$_2$CH$_3$; 1.3(12H) intermediate (CH$_2$)$_6$ of octyl; 1.6 (m) (6H)SiCH$_2$CH$_2$ and OCH$_2$CH$_2$CH$_2$; 3.4(4H) OCH$_2$ $^{29}$Si NMR (CDCl$_3$):+17.5(s)=SiOH

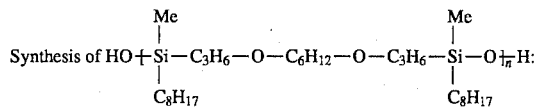

The above hybrid disilanol compound (3c) was condensed to a polymer under an argon atmosphere by refluxing in toluene for three days in the presence of tetramethylguanidine trifluoroacetate, as in the preparation of the polymer of Example 1.

The following structure was obtained in 95% yield

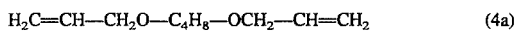

The polymer (3d) had a glass transition temperature of −82° C. and any first order transition did not appear upon DSC analysis. A number average molecular weight of 12,000 (GPC using polystyrene calibration) was measured (this corresponds to an average DP of n=22). The $^{29}$Si NMR spectrum of (3d) showed a peak at +7.1 ppm (s) in CDCl$_3$, in agreement with a polymeric structure containing the group C—Si—O—Si—C.

Example 4

Following the procedure of Example 3, but starting from diallyl ether of the formula H$_2$C=CH—CH$_2$O—C$_4$H$_8$—OCH$_2$—CH=CH$_2$ (4a)

and methyl octyl dihydrosilane of the formula

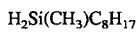

H$_2$Si(CH$_3$)C$_8$H$_{17}$ there was prepared the telechelic hybrid-organo-dihydro silane of formula

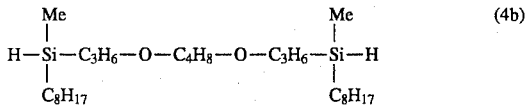

obtained in 80% yield, which by analysis showed IR, $^1$H NMR and $^{29}$Si NMR spectra similar to those of compound (3b) of example 3. The above hybrid dihydro silane (4b) was hydrolyzed as in Example 3 in the presence of a buffer solution of NaH$_2$PO$_4$ and 0.1N NaOH, and yielded 93% of the telechelic hybrid-organo-disilanol of the formula

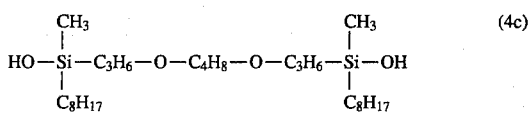

which showed IR, $^1$H NMR and $^{29}$Si NMR spectra similar to those of compound (3c) of Example 3. The hybrid disilanol (4c) was condensed, as in Example 3, in the presence of tetramethylguanidine trifluoroacetate to give the hybrid-sila-organo-siloxane polymer of the formula:

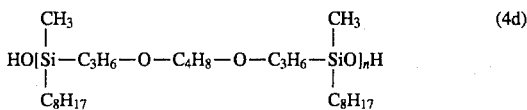

The polymer (4d) had a glass transition temperature of −85° C. and no first order transition was observed. A number average molecular weight corresponding to an average DP of n=20 was measured. The $^{29}$Si NMR spectrum showed a peak at +7.2 ppm (s), in agreement with a polymeric structure containing the group C—Si—O—Si—C.

That which is claimed is:

1. A method for preparing a hybrid organodisilanol compound having the formula

HO—R$^1$R$^2$SiC$_n$H$_{2n}$RC$_n$H$_{2n}$SiR$^1$R$^2$—OH  (I)

said method comprising:
   (A) reacting a dihydridosilane of the formula

R$^1$R$^2$SiH$_2$  (II)

with a diene of the formula

C$_n$H$_{2n-1}$RC$_n$H$_{2n-1}$  (III)

to provide a dihydrido compound of the formula

H—R$^1$R$^2$SiC$_n$H$_{2n}$RC$_n$H$_{2n}$SiR$^1$R$^2$—H  (IV);

and
   (B) reacting said dihydrido compound (IV) with a buffered water solution in the presence of a palladium catalyst, wherein
   R$^1$ and R$^2$ are independently selected from the group consisting of alkyl radicals having 1 to 12 carbon atoms, phenyl, halogenated alkyl radicals having 3 to 12 carbon atoms, alkylphenyl radicals and monovalent radicals derived from telomers or cotelomers of fluorinated organic monomers, with the proviso that there is no more than one phenyl group per silicon atom in formulas (I), (II) or (IV),
   n is 2 or 3 and
   R is a divalent organic group selected from the group consisting of
   (a) —O(C$_t$H$_{2t}$O)$_m$— wherein t is an integer having a value of 2 to 12 and m is an integer having a value of 1 to 6;
   (b) branched or linear divalent hydrocarbon groups having 2 to 12 carbon atoms;
   (c) branched or linear divalent fluorohydrocarbon groups; and
   (d) derivatives of alkylene-terminated telechelic divalent telomers or cotelomers.

2. The method according to claim 1, wherein R$^1$ and R$^2$ are independently selected from the group consisting of monovalent radicals derived from telomers of fluorinated organic olefins and monovalent radicals derived from cotelomers of fluorinated organic olefins.

3. The method according to claim 2, wherein $R^1$ and $R^2$ are independently selected from the group consisting of
(i) alkylene-terminated monovalent homotelomers selected from the group consisting of telomers of chlorotrifluoroethylene, tetrafluoroethylene, vinylidene fluoride and trifluoroethylene;
(ii) cotelomers of chlorotrifluoroethylene and hexafluoropropene;
(iii) cotelomers of tetrafluoroethylene and one member selected from the group consisting of hexafluoropropene, 1-H-pentafluoropropene and 2-H-pentafluoropropene;
(iv) cotelomers of vinylidene fluoride and one member selected from the group consisting of hexafluoropropene and pentafluoropropene;
(v) cotelomers of tetrafluoroethylene and a perfluoroalkyl vinyl ether;
(vi) cotelomers of tetrafluoroethylene, chlorotrifluoroethylene and a perfluoroalkyl vinyl ether; and
(vii) cotelomers of tetrafluoroethylene, chlorotrifluoroethylene and hexafluoropropene.

4. The method according to claim 1, wherein R is selected from the group consisting of divalent fluorohydrocarbon groups, derivatives of telechelic divalent fluorotelomers and derivatives of telechelic divalent fluorocotelomers.

5. The method according to claim 4, wherein R is represented by the formula

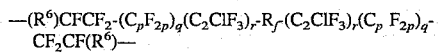

in which $R_f$ represents a perfluoroalkylene radical containing from 2 to 6 carbon atoms, $R^6$ is selected from the group consisting of fluorine and trifluoromethyl, the value of p is 2 or 3, r is 0 or a positive integer from 1 to 6, q is 0 or a positive integer from 1 to 6 and (r+q) is from 2 to 12.

6. The method according to claim 1, wherein said palladium catalyst is supported on alumina.

7. The method according to claim 1, wherein said dihydrosilane (II) is prepared by reacting a diorganodihalosilane having the structure $R^1R^2SiCl_2$ with lithium aluminum hydride, in which $R^1$ and $R^2$ are independently selected from the group consisting of alkyl radicals having 1 to 12 carbon atoms, halogenated alkyl radicals having 3 to 12 carbon atoms, phenyl, $C_{1-C4}$ alkyl-phenyl radicals, monovalent radicals derived from telomers of fluorinated organic olefins and monovalent radicals derived from cotelomers of fluorinated organic olefins, with the proviso that there is no more than one phenyl group per silicon atom in said diorganodihalosilane.

8. The method according to claim 1, wherein R is selected from the group consisting of

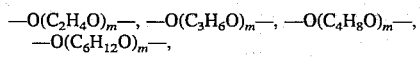

in which m is an integer having a value of from 1 to 3, and divalent hydrocarbon groups having from 2 to 8 carbon atoms.

9. The method according to claim 8, wherein $R^1$ and $R^2$ are independently selected from the group consisting of alkyl radicals having 1 to 12 carbon atoms, phenyl and halogenated alkyl radicals having 3 to 12 carbon atoms.

10. A hybrid-sila-organo-polysiloxane comprising —A— units and, optionally, —B— units, wherein —A— is $-R^1R^2SiC_nH_{2n}RC_nH_{2n}SiR^1R^2O-$, —B— is selected from the group consisting of $-R^{1a}R^{2a}SiO-$ and $-R^{1a}R^{3a}SiO-$, $R^1$ and $R^2$ are independently selected from the group consisting of $C_1-C_{12}$ alkyls, phenyl and alkylphenyl, $-C_nH_{2n}-$ is a linear divalent radical in which n is 2 or 3, R is selected from the group consisting of:
a1) $-O(C_tH_{2t}O)_m-$, in which t is an integer from 2 to 12, m is an integer from 1 to 6, with the proviso that no more than one phenyl group per silicon atom is present in the repeating unit —A— and
b1) a divalent hydrocarbon group having from 2 to 8 carbon atoms, with the proviso that in the repeating unit —A— no more than one phenyl group and no more than one methyl group per silicon atom is present and with the proviso that when $R^1$ is methyl then $R^2$ is selected from the group consisting of a $C_5-C_{12}$ alkyl, phenyl and $C_1-C_4$ alkylphenyl,
$R^{1a}$ and $R^{2a}$ are monovalent radicals independently selected from the group consisting of $C_1-C_{12}$ alkyl, $C_3-C_{12}$ halogenated alkyl, phenyl, alkylphenyl, telomers of fluorinated organic olefins and cotelomers of fluorinated organic olefins and $R^{3a}$ is an alkenyl radical.

11. The hybrid-sila-organo-polysiloxane according to claim 10, which is represented by a main chain formula selected from the group consisting of $(A)_x$, $(AB)_x$, $(ABA)_x$ and $(BAB)_x$, wherein A is $-R^1R^2SiC_nH_{2n}RC_nH_{2n}SiR^1R^2O-$, B is selected from the group consisting of $-R^{1a}R^{2a}SiO-$ and $-R^{1a}R^{3a}SiO-$, $R^1$ and $R^2$ are independently selected from the group consisting of $C_1-C_{12}$ alkyls, phenyl and alkylphenyl, $-C_nH_{2n}-$ is a linear divalent radical in which n is 2 or 3, R is selected from the group consisting of:
a1) $-O(C_tH_{2t}O)_m-$, in which t is an integer from 2 to 12, m is an integer from 1 to 6, with the proviso that no more than one phenyl group per silicon atom is present in the repeating unit —A— and
b1) a divalent hydrocarbon group having from 2 to 8 carbon atoms, with the proviso that in the repeating unit —A— no more than one phenyl group and no more than one methyl group per silicon atom is present and with the proviso that when $R^1$ is methyl then $R^2$ is selected from the group consisting of a $C_5-C_{12}$ alkyl, phenyl and $C_1-C_4$ alkylphenyl,
$R^{1a}$ and $R^{2a}$ are monovalent radicals independently selected from the group consisting of $C_1-C_{12}$ alkyl, $C_3-C_{12}$ halogenated alkyl, phenyl, alkylphenyl, telomers of fluorinated organic olefins and cotelomers of fluorinated organic olefins, $R^{3a}$ is an alkenyl radical and x has an average value of 10 to 1,000.

12. The hybrid-sila-organo-polysiloxane according to claim 10, wherein R is selected from the group consisting of the structures $-O(C_2H_4O)_m-$, $-O(C_3H_6O)_m-$, $-O(C_4H_8O)_m-$ and $-O(C_6H_{12}O)_m-$, in which m is from 1 to 3.

13. The hybrid-sila-organo-polysiloxane according to claim 10, wherein R is selected from the group consisting of branched or linear divalent hydrocarbon groups having from 2 to 4 carbon atoms.

14. In a method for lubricating a substrate comprising applying a lubricant to at least a portion of said substrate, the improvement comprising using the hybrid-sila-organo-polysiloxane of claim 10 as said lubricant.

15. In a method for sealing a joint comprising applying a curable sealant to the joint and curing the sealant the improvement comprising using a curable sealant prepared from the hybrid-sila-organo-polysiloxane of claim 10.

16. A cured rubber composition prepared from the hybrid-sila-organo-polysiloxane of claim 10.

* * * * *